United States Patent [19]

Filhol

[11] 4,449,630
[45] May 22, 1984

[54] PACKAGE FOR DENTAL TOOLS
[76] Inventor: Stuart J. Filhol, Castlefreke, County Cork, Ireland
[21] Appl. No.: 340,479
[22] Filed: Jan. 18, 1982
[51] Int. Cl.³ .................... B65D 85/24; B65D 85/20
[52] U.S. Cl. .................................. 206/369; 206/379; 206/380; 206/533; 206/443; 221/256; 221/277
[58] Field of Search ............. 206/369, 379, 533, 380, 206/443; 221/82, 255, 256, 277

[56] References Cited
U.S. PATENT DOCUMENTS

| | | | |
|---|---|---|---|
| 1,026,860 | 5/1912 | Hamilton | 206/443 |
| 2,573,311 | 10/1951 | Cupler | 206/379 |
| 3,297,198 | 1/1967 | Wright, Jr. | 221/82 |
| 4,203,518 | 5/1980 | Current | 206/533 |

FOREIGN PATENT DOCUMENTS 465353  5/1950  Canada .................. 221/256

Primary Examiner—William T. Dixson, Jr.
Assistant Examiner—Brenda J. Ehrhardt
Attorney, Agent, or Firm—Gifford, VanOphem, Sheridan, Sprinkle & Nabozny

[57] ABSTRACT

A package for articles is particularly suitable for small dental tools and fittings.

The package includes a base member and a rotary member mounted for rotation relative to the base member.

A circular space for the articles is defined between the base member and the rotary member and the space is divided into radial compartments arranged to receive the articles.

The base member also defines a chute leading to a pocket, the chute communicating with the compartments for dispensing the articles upon rotation of the rotary member.

The rotary member is transparent for viewing the articles in the compartments and the rotary member is indexable to ensure retention and release of articles from the compartments.

10 Claims, 3 Drawing Figures

PACKAGE FOR DENTAL TOOLS

This invention relates to a package for retaining, storing and dispensing articles, in particular, small articles.

Storing and dispensing small articles, such as dental pins for use in dentistry, can be a particular problem especially when such articles have to be stored hygenically and be made available for use quickly and without removing wrappings. Moreover it is advantageous if the packaging for the articles is able to contain a stock of the articles for ready release from the package by the operator individually and one-handed, if necessary, without great risk of the articles falling out of the package inadvertently.

It is an object of the invention to provide a package in the nature of a magazine for retaining, storing and dispensing small articles whereby the articles are readily released individually and in which the articles are presented in an attractive manner.

According to the invention a package for small articles comprises a base member, a rotary member carried on the base member for rotation relative to the base member, a circular space defined between the base member and the rotary member and compartments in said space extending radially of the axis of rotation of the rotary member, the radial compartments being arranged to contain the articles, and the base member defining an outlet chute leading to a receiving pocket and communicating with said space whereby the radial compartments are aligned with the chute upon rotation of the rotary member to enable articles in said compartments to be passed along the chute to said pocket.

Preferably the compartments are elongate and extend from the radially inner to the radially outer sides of said space to accommodate elongate articles, for example, dental pins.

Conveniently the rotary member is formed with integral radially extending portions defining the radial compartments and as the rotary member is rotated the articles are carried around the space towards the chute. The radially extending portions may include elongate, tapered members tapering in the radially inwards direction so that said members are narrower towards their radially inner ends.

The rotary member may have indexing means whereby the compartments are readily aligned with said chute.

Further features of the invention appear from the following description of an embodiment of the invention given by way of example only and with reference to the drawings, in which.

Figure 1:
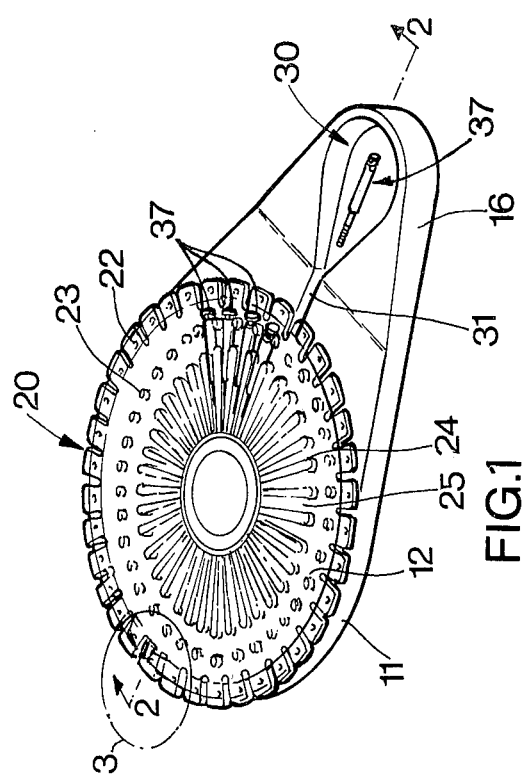
FIG. 1 is a perspective view of a package according to the invention.

Referring to the drawings a package, particularly suitable for dental pins, is shown. The package includes a base member 10 which in this case is a plastics molding of opaque plastics. The base member 10 has a generally circular portion 11 and an extension 16 from one side of the circular portion. The circular portion 11 defines a circular space 12 having a peripheral lip 13, the top of the lip being recessed at 14 and there being an inner stepped portion 15 adjacent the lip 13.

At the axis of the circular portion is a hub portion 17 defining an axial opening 18. A pivot pin 19 extends through the opening 18 and rotatably supports and secures a rotary member 20 on the base member 10.

The rotary member 20 is generally circular and is made of a transparent plastics molding so that articles located within the space 12 can be viewed through the member 20.

Around the outer edge of the rotary member 20 are formed a plurality of equal-spaced slots 21 extending from the outer edge in a radially inwards direction. Directed downwardly from the portions of the member 20 between the slots 21 are integral projections 22 which serve to assist in indexing the member 20 about its axis, as will be described. Aligned with the projections 22 in the radial direction and located inwardly thereof are further circular integral projections 23. Spaced radially inwards of the projections 22 and 23 are integral elongate portions 24 of the member 20 which are tapered inwardly in the radially inwards direction to extend up towards the hub portion 17 of the base member 10. The projections 23 and elongate portions 24 are regularly spaced circumferentially of the member 20 and define a plurality of radial compartments 25 around the member 20. Due to the portions 24 being narrower at their radially inner ends the widths of the compartments are wide enough at such ends to accommodate the articles.

The extension 16 of the base member 10 is shaped to define a pocket 30 which is tear drop-shaped and at its narrower end communicates with a chute 31 which lies radially of the rotary member 20 so as to be aligned with the compartments 25 as the member 20 is rotated. The pocket 30 is bounded by a wall 32 which increases in height towards the wider end of the pocket by increasing the depth of the base member 10 in that region. This serves to ensure that the articles passing along the chute 31 into the pocket 30 are less liable to fall out of the pocket.

The rotary member 20 is rotated about its axis to release articles in the compartments 25 along the chute 31 and into the pocket 30. To afford controlled movement of the rotary member 20 for this purpose, indexing means is provided between the rotary member 20 and the base member 10. Such indexing means comprises the projections 22 on the member 20 which normally pass freely along the recess 14 in the lip 13 of the base member 10. At a position opposite the chute 31 the recess 14 is formed with inclined ramps 34 between which is formed a recess 35 in which the projections 22 are engageable when a compartment 25 is aligned with the chute 31. Such projections 22, ramps 34 and the recess 35 provide a resistance to rotation of the rotary member 20 in a position in which the articles in the compartments 25 can be dispensed into the pocket 30 and in a position in which a compartment 25 is displaced from the aligned position. This serves to ensure alignment of the compartments 25 with the chute 31 to enable the articles to be easily passed along the chute 31 and, in the displaced position, it ensures that articles are not inadvertently dispensed into the pocket 30.

Various kinds of articles may be contained in and dispensed from the package but the package is especially suited to dental pins, drills, burrs and like dental tools which are elongate and relatively small and difficult to handle. In practice the dental tools, such as pins, would be sold contained within the package and the pins would be dispensed as required by the dentist. This is achieved simply by viewing the package to see through the transparent rotary member 20 the pin required, aligning the compartment 25 containing the pin with the chute 31 and then tipping the package so that the pin slides out of the compartment 25 into and along the chute 31 to be received in the pocket 30. The shape of the pocket 30 readily enables the pin to be removed from the pocket 30. It will be seen that the rotary member 20 can be readily turned one-handed, if necessary, to leave one hand of the operator free, for example, to hold the dental handpiece into which the pin is to be fitted.

Figure 3:
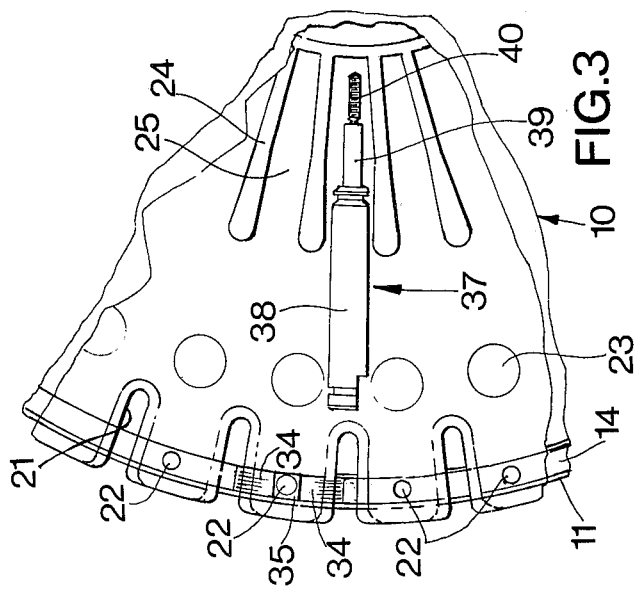
FIG. 3 is an enclosed plan view of the part of the package designated 3 in FIG. 1 showing another form of article.

The package is capable of containing and dispensing different kinds of dental pins. In FIG. 3 there is illustrated one such pin 37 for which the package is suitable. The pin 37 has a connecting portion 38 by which the pin 37 is connected to a dental handpiece, a cylindrical shank portion 39 and a threaded pin portion 40 which is detachably connected to the shank portion 39. The narrower pin and shank portions 40 and 39 are located at the radially inner end of the compartments 25.

Figure 2:
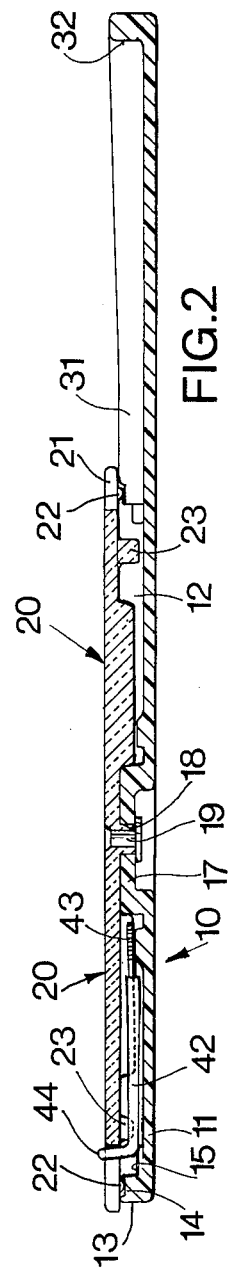
FIG. 2 is a section on the line 2—2 in FIG. 1 to a larger scale showing one form of article.

An alternative form of pin 42 is shown in FIG. 2. The pin 42 is generally cylindrical having a detachable threaded pin portion 43 at one end and a turned over shank portion 44 at the other end. It will be seen that the turned over portion 44 projects through the radially inner end of the slot 21 associated with the respective compartment 25.

It will be appreciated that the package provides a container which securely retains the articles in a hygenic condition ready for easy and rapid dispensing of the articles. Moreover the package has an attractive appearance and is simply made and stored.

What I claim as my invention and desire to secure by Letters Patent of the United States is:

1. A package for articles comprising a base member, a rotary member carried on the base member for rotation relative to the base member, a circular space defined between the base member and the rotary member, and compartments in said space extending radially of the axis of rotation of the rotary member, the radial compartments being defined by radially directed portions of the rotary member and being arranged to contain the articles, and the base member defining an outlet chute leading to a receiving pocket and communicating with said space whereby each of the radial compartments is able to be aligned in registration with the chute upon rotation of the rotary member to enable an article in a compartment in registration with the chute to be passed from the compartment into the receiving pocket.

2. A package according to claim 1 wherein the base member, the chute and the pocket lie in a common plane and the pocket extends generally outwardly of the periphery of the rotary member.

3. A package according to claim 1 wherein the compartments are elongate to accommodate elongate articles which extend radially of the axis of rotation of the rotary member.

4. A package according to claim 1 wherein said portions include elongate tapered members which taper in the radially inwards direction so that said tapered members are narrower towards their radially inner ends.

5. A package according to claim 1 comprising indexing means defined by the rotary member and the base member whereby upon rotation of the rotary member each indexed position of the rotary member aligns a compartment with said chute.

6. A package according to claim 5 wherein the indexing means comprises projections on the rotary member corresponding to the location of the radial compartments and a recess in the base member arranged to be engaged by the projections whereby when a projection engages the recess there is a resistance to rotation of the rotary member.

7. A package according to claim 1 wherein the rotary member projects radially outwardly relative to the base member.

8. A package according to claim 1 wherein the radially outer edge of the rotary member is formed with radially directed slots aligned with the compartments.

9. A package according to claim 1 wherein said pocket is wider in a direction away from the portion of the pocket communicating with said chute.

10. A package according to claim 1 wherein the rotary member is formed of transparent material.

* * * * *